United States Patent [19]

Mark

[11] Patent Number: 5,247,706
[45] Date of Patent: Sep. 28, 1993

[54] FACE SHIELD DETACHABLY MOUNTED TO SPECTACLES

[76] Inventor: Phillip E. Mark, 4505 131st Ave. North, #8, Clearwater, Fla. 34622

[21] Appl. No.: 922,446

[22] Filed: Jul. 30, 1992

[51] Int. Cl.$^5$ .......................... G02C 9/04; A61F 9/04
[52] U.S. Cl. ................................................ 2/9; 2/13; 2/427; 2/444; 351/158
[58] Field of Search ................. 2/9, 10, 444, 8, 427, 2/13; 351/155, 158

[56] References Cited

U.S. PATENT DOCUMENTS

| | | | |
|---|---|---|---|
| 2,610,323 | 9/1952 | Johnson | 2/8 |
| 3,051,957 | 9/1962 | Chan | 351/155 X |
| 4,592,096 | 6/1986 | Glasheen | 2/427 |
| 4,924,526 | 5/1990 | Parissenti et al. | 2/13 |
| 4,965,887 | 10/1990 | Paoluccio | 351/158 X |

Primary Examiner—Peter Nerbun
Attorney, Agent, or Firm—Joseph C. Mason, Jr.; Ronald E. Smith

[57] ABSTRACT

A face shield assembly is releasably attached to a pair of spectacles and is adjustable so that it may be placed close to or away from the wearer's face. It is lockable into each position of adjustment. Multiple apertures are formed in a clear or tinted lens, just below its uppermost edge, and these apertures press fittingly receive posts that are formed along the length of a flexible base member that conforms to the contour of the wearer's head so that the lens depends from the base member. The opposite ends of the lens are retained in detent members formed in the opposite ends of the base member, and a horizontal top shield extends from the base member to the wearer's forehead.

12 Claims, 3 Drawing Sheets

FACE SHIELD DETACHABLY MOUNTED TO SPECTACLES

BACKGROUND OF THE INVENTION

1. Field of the invention

This invention relates, generally, to devices for shielding the human face. More particularly, it relates to a face shield that is releasably attachable to a pair of spectacles.

2. Description of the prior art

Face shields are now in common use by healthcare personnel who want to prevent blood or other body fluids from splashing onto their face. Numerous designs have been developed, but the known designs are either built into a helmet or other head gear, or are substantially permanently attached to a pair of spectacles.

Typical face shields of complex construction are shown in U.S. Pat. Nos. 4,821,340, 4,843,643, 4,924,526, and 4,945,573 .

The device shown in U.S. Pat. No. 4,924,526 includes a transparent shield that must be attached to a pair of spectacles or a spectacle substitute having no lens. Attachment of the shield to the spectacles requires a permanent modification of the spectacles, and a tool must be used to replace the shield if it becomes cracked or soiled; thus, quick and trouble-free replacement of the shield is not provided. Moreover, the shield is mounted at a fixed, non-adjustable distance from the wearer's face.

In other known shield assemblies, the shield part thereof is an integral part of the device; thus, if the shield becomes cracked or splattered with fluids, the entire unit must be discarded. Thus, there remains a need for an adjustable face shield that includes a detachable shield part that can be replaced as needed. Moreover, the replacement task, ideally, should be easy, quickly accomplished, and should not require the use of tools.

At the time the present invention was made, the prior art, when considered as a whole, neither taught nor suggested to those of ordinary skill in this art how the needed face shield could be provided.

SUMMARY OF THE INVENTION

The longstanding but heretofore unfulfilled need for a face shield having an adjustable, quickly and easily replaceable shield that is releasably attachable to a pair of spectacles without requiring modification of the spectacles is now provided. A flexible plastic shield has a plurality of laterally spaced apertures formed therein, just below and along the extent of its uppermost edge, and these apertures pressfittingly receive a corresponding plurality of posts that are carried by a flexible base member that conforms, generally, to the shape of a human head. In this manner, the shield depends from the base member and protects the wearer's face. The press fit engagement between the apertures and their associated posts enables facile replacement of the shield without tools as needed; moreover, the base member and other parts of the novel device need not be discarded when a shield is changed.

A horizontal top shield substantially closes the gap between the shield and the wearer's forehead.

Means are also provided for attaching the face shield assembly to a pair of spectacles in a quick release fashion. A spring-loaded clip is mounted in bridging relation to a trailing end of a pair of parallel, "L"-shaped mounting members, and that clip releasably engages the spectacles worn by the individual wearing the face shield; the wearer either attaches the novel assembly to his or her regular glasses or uses spectacles having prescription-free lens if said wearer's vision does not require correction or if contacts are worn.

The second end of each "L"-shaped mounting member is slidably and adjustably connected to a channel-defining means secured to the top shield so that the base member and hence the shield depending therefrom are movable toward and away from the user's face as desired. The shield is lockably held in each position of adjustment. A pair of laterally spaced flange members are also provided to inhibit rotational bending of the "L"-shaped mounting members.

An important object of this invention is to advance the art of face shields by providing a face shield of elegant construction.

Another important object is to provide a face shield assembly where the shield part thereof is easily replaceable.

Still another object is to provide a face shield assembly that is easily attachable to a pair of glasses in the absence of tools.

These and other objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
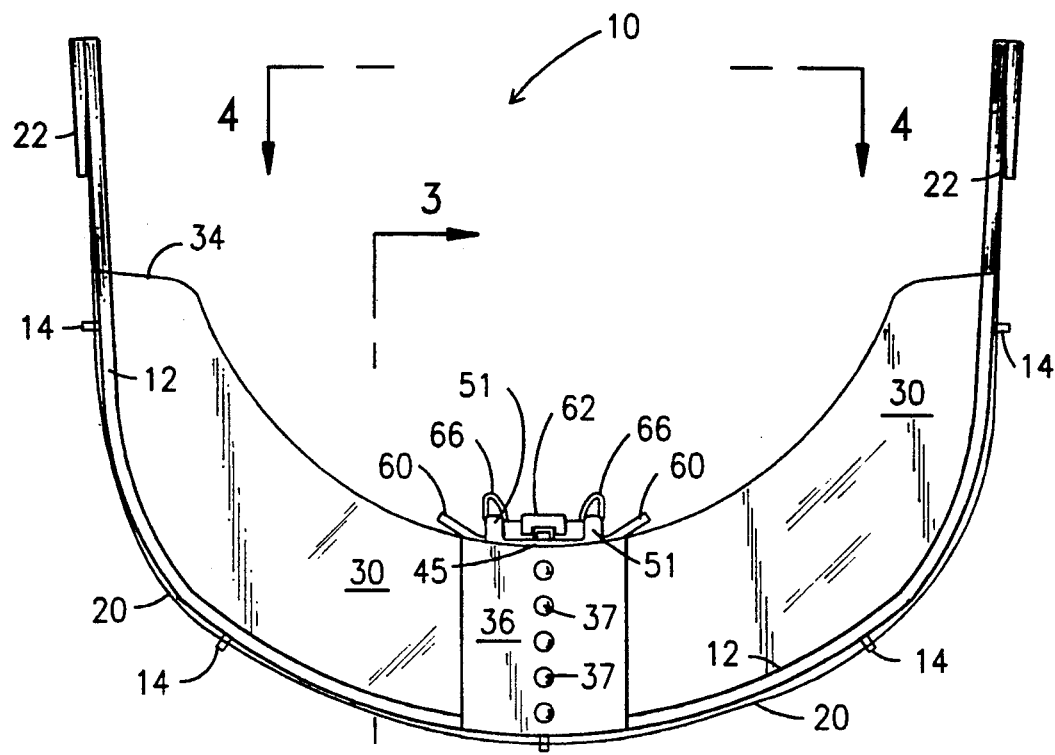
FIG. 1 is a top plan view of the novel face shield.
Figure 2:
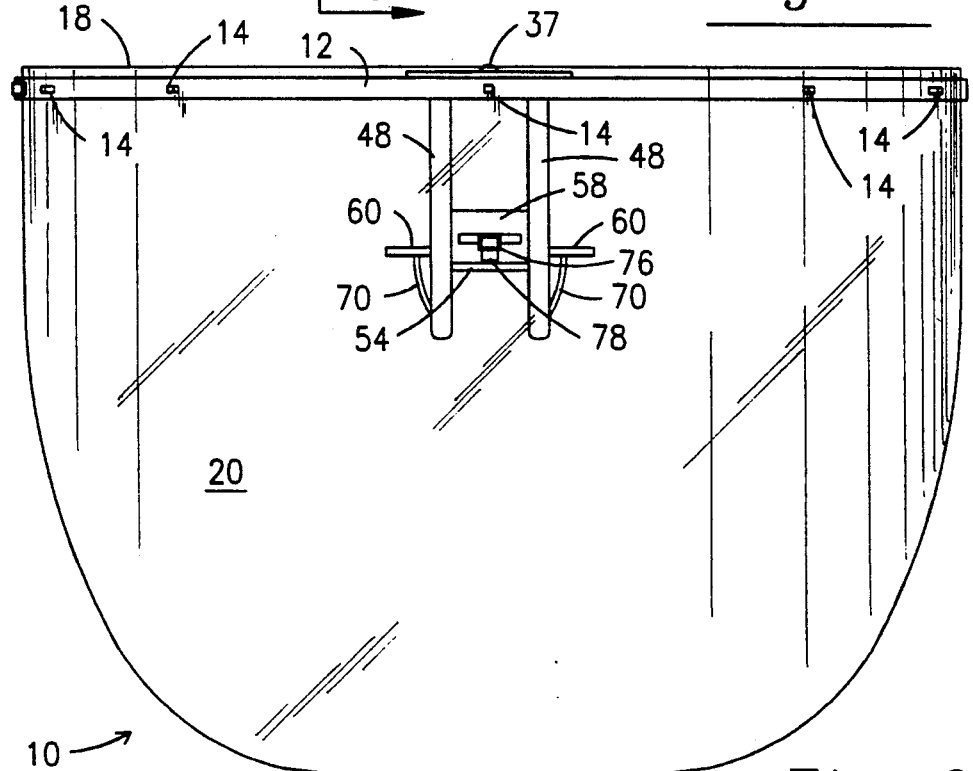
FIG. 2 is front elevational view thereof.

Referring now to FIG. 1, it will there be seen that an illustrative embodiment of the invention is denoted as a whole by the reference numeral 10.

Face shield assembly 10 includes a flexible base member 12 having posts 14 formed therein along the extent thereof in equidistantly spaced relation to one another. Each of these posts press fittingly engages an associated aperture formed in flexible shield 20 just below the uppermost edge 18 thereof. Shield means 20 is formed of a plastic or other suitable material; it may be clear or tinted.

The opposite ends of the shield means 20 are releasably engaged by detent members 22, 22, each of which includes a slot that slidably receives its associated edge of said shield means. Accordingly, attachment of a new shield means 20 to base member 12 is easily accomplished; a first preselected edge of the shield means 20 is slipped into a slot defined by a detent 22, the shield means is wrapped around the base member 12 so that posts 14 engage their associated apertures 16, and the second edge of the shield means is slipped into its slot at the opposing detent; this completes the attachment procedure. Removal of a shield means is just as easily accomplished by reversing those steps.

A top shield means 30, preferably formed of the same material as shield means 20, is fixedly secured by an adhesive or other suitable means to base member 12, in trailing relation thereto. More particularly, the leading edge 32 of top shield means 30 has the same curvature as the base member 12 and is coincident therewith. The trailing edge 34 of said top shield means has a slightly different curvature, as shown.

Top shield means 30 provides the mounting base for the assembly that releasably secures the face shield assembly 10 to a pair of spectacles. That assembly includes flat plate 36 that is fixedly secured to the bight region of top shield 30 in overlying relation thereto by adhesive or other suitable means. A plurality of hemispherical protuberances, collectively denoted 37, are formed in linear array atop flat plate 36; each of said dome-shaped protuberances is hollow.

Figure 4:
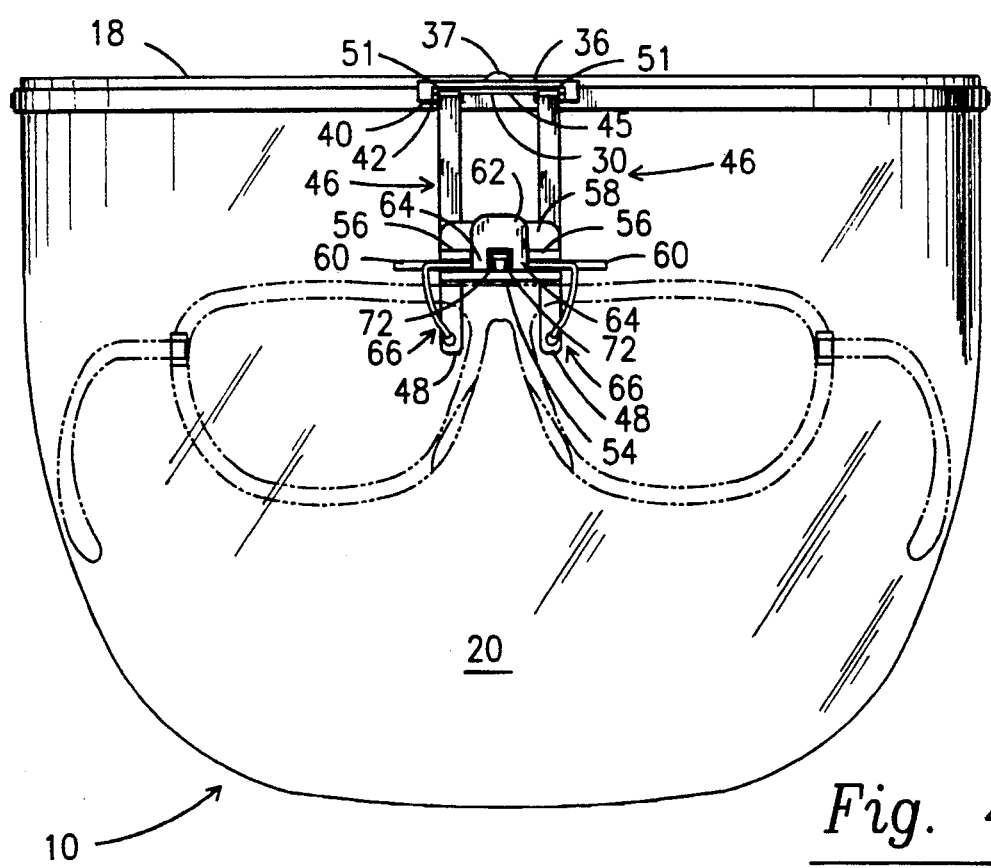
FIG. 4 is a rear elevational view thereof.
Figure 5:
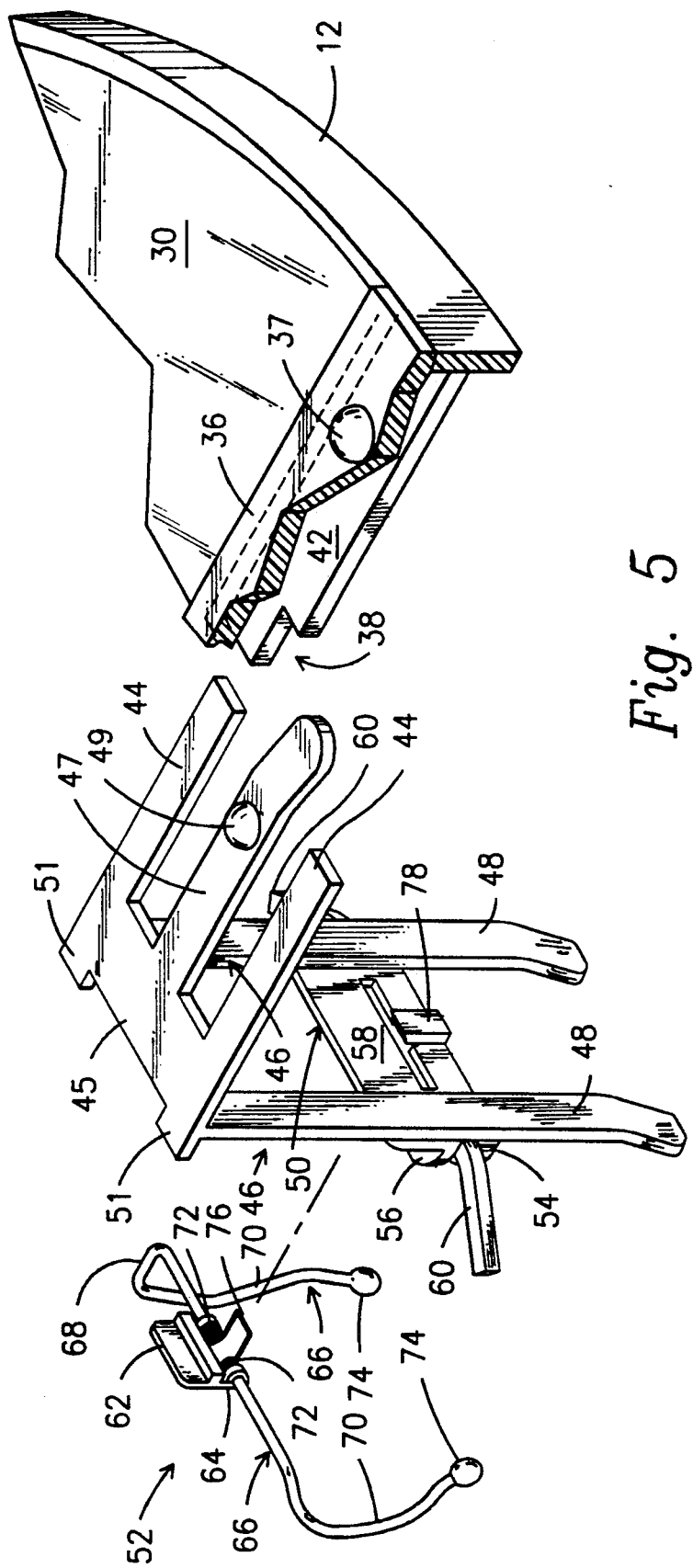
FIG. 5 is an exploded perspective view of the clip assembly.

A pair of parallel, longitudinally aligned, transversely spaced apart channel-defining members 38, only one of which is shown in FIG. 5, are secured to the underside of top shield means 30, in transversely spaced apart relation to one another; the spacing is such that the outermost edges of the respective channel-defining members 38 is flush with the outermost edges of flat plate 36, as will become clear in connection with the description of FIG. 4 below. Thus, top shield 30 is held in sandwiched relation between said flat plate 36 and channel-defining members 38.

As perhaps best depicted in FIG. 4, each channel-defining member 38 includes a sidewall 40, that is adhered to the underside of top shield 30, and a bottom wall 42; the opposing bottom walls 42 extend a short distance toward one another as shown in FIGS. 4 and 5 so that each sidewall 40 and its associated bottom wall 42 defines a channel. Opposing bottom walls 42 could be provided in the form of a single piece bottom wall having the same transverse extent as flat plate 36, but materials are saved by limiting the transverse extent of the opposing bottom walls as depicted.

Each channel slidably receives the first or leading end 44 (FIGS. 3 and 5) of an "L"-shaped member 46.

Bridge 45 interconnects parts 44, and flexible and resilient locking platform 47 extends forwardly from said bridge, in parallel and coplanar relation to parts 44. A hemispherical protuberance 49 is formed in locking platform 47, and it enters into and lockingly engages a preselected protuberance 37 formed in flat plate 36 when the novel faceshield is in use. Platform 47 is shown fully inserted in FIG. 3; this represents the closest positioning of faceshield 20 to the user's face.

Figure 3:
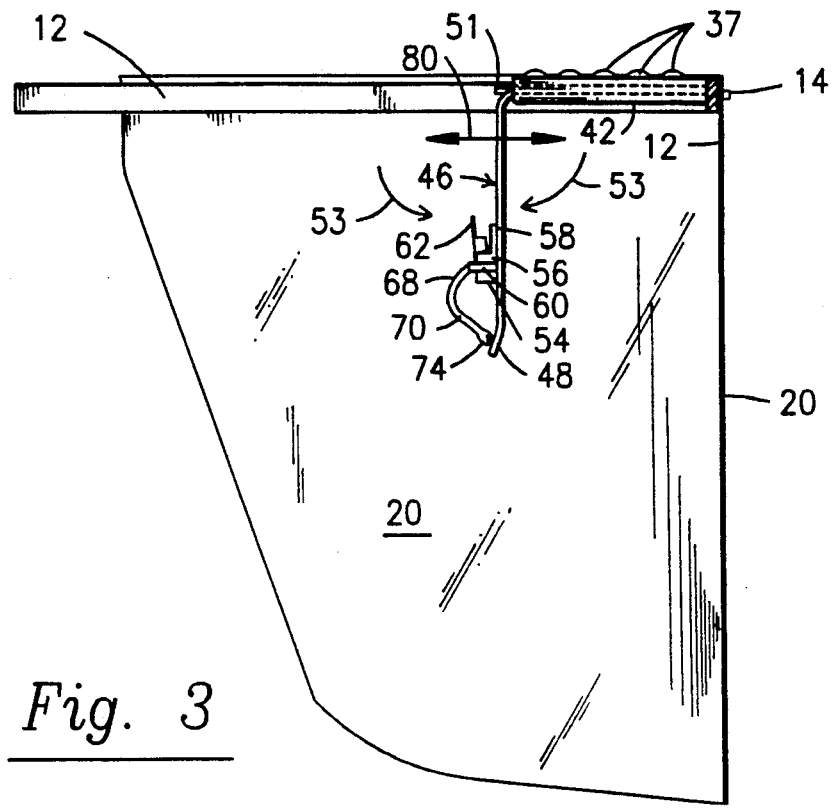
FIG. 3 is a side elevational view thereof.

Trailing flanges 51, best shown in FIG. 5, inhibit rotational movement, as indicated by arrows 53 in FIG. 3, between parts 44 and 48 of member 46.

The respective trailing or second ends 48 of member 46 are interconnected by bridge member 50, best shown in FIG. 5. Bridge member 50 serves to maintain the transverse spacing of parts 48 and further serves to hold clip means 52. More particularly, bridge 50 includes a bottom wall 54 that is disposed orthogonally with respect to strips 48, a pair of transversely spaced apart top walls 56 disposed in parallel alignment with bottom wall 54, and a back wall 58. A spacer means 60 serves to position clip 52 above the plane of back wall 58 to allow operation of said clip.

More particularly, clip 52 includes a plate 62 having a pair of depending, transversely spaced legs 64, each of which has a return bend formed in its distal free end for securely gripping a first end of its associated clamping member 66. Each clamping member 66 has two bends formed therein, the first bend 68 projecting generally rearwardly with respect to shield means 20, and downwardly with respect to top shield 30, as best shown in FIG. 3, and the second bend 70 projecting generally downwardly and forwardly when assembly 10 is being worn. The respective proximal ends of each clamping member 66 are tightly clamped by the return bend formed in each depending leg 64 so that pivotal movement of plate 62 and legs 64 effects simultaneous and corresponding movement of each clamping member 66. Each proximal end has an innermost end that extends inwardly of its associated return bend, and the coiled central part of torsion spring 72 (FIG. 5) is rotatably mounted thereto. The distal free ends 74 of legs 66 are bulbous and made of a soft, non-scratching material to avoid scratching the lens of the spectacles. The torsion springs 72 are interconnected by an anchor means 76 (also FIG. 5) that wraps around and thereby engages stop member 78 that is secured to and which projects upwardly from the leading edge of bottom wall 54 and spacer means 60. The distal free end of each torsion spring 72 bears against the leading side of plate 62; thus, bulbous ends 74 of legs 66 bear against their associated flat strip trailing ends 48 when the springs are in repose, thereby holding the entire face shield assembly 10 to said spectacles when the leading ends 44 of flat strips 46 are slidably received within their associated channels 38.

As indicated in FIG. 3 by the double-headed reference numeral 80, it is a simple matter to slide shield 20 toward or away from the user's face as desired. As mentioned earlier, the interlocking of dome-shaped members 37 and 49 provides a positive lock in each position of adjustment.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:
1. A face shield assembly, comprising:
a flexible base member;
said base member having a curvature formed therein so that it follows the contour of a human head;
a plurality of posts spaced at predetermined intervals along the length of said base member;
a flexible shield means;
a plurality of apertures formed in said flexible shield means near an uppermost edge thereof so that said flexible shield means is detachably secured to said base member by press fitting said posts into their associated apertures;

a top shield means having a leading edge that conforms to the curvature formed in said base member and that is fixedly secured thereto, said top shield means substantially closing a space between the base member and the user's forehead when the face shield assembly is worn;

a clamp means that detachably engages a pair of spectacles having lens means; and engagement means for releasably attaching said top shield means to said clamp means;

detent means at opposite ends of said base member for releasably retaining opposite ends of said flexible face shield against said base member so that the shape of said flexible shield means conforms to the shape of said base member; and said engagement means including means for slideably engaging said top shield means and for engaging said clamp means so that said flexible shield means may be placed at differing spacings relative to the face of the user of said face shield.

2. The face shield of claim 1, wherein said engagement means further includes a flat plate secured to said top shield in overlying relation thereto at a bight region thereof.

3. The face shield of claim 2, wherein said engagement means further includes a pair of transversely spaced apart channel-defining members fixedly secured to an underside of said top shield means so that said top shield means is disposed in sandwiched relation between said flat plate and said channel-defining members.

4. The face shield of claim 3, wherein said engagement means further includes a pair of transversely spaced apart "L"-shaped flat members, each member of said pair of flat members having a leading end and a trailing end, each leading end being disposed substantially orthogonally with respect to its associated trailing end, and each of said leading ends being slidably disposed within an associated channel-defining member of said pair of channel-defining members.

5. The face shield of claim 4, further comprising a first bridge member for interconnecting the leading ends of said flat members, and a second bridge member for interconnecting the trailing ends of said flat members, said first and second bridge members also maintaining the transversely spaced relation between said leading and trailing ends, respectively.

6. The face shield of claim 5, further comprising a flexible platform member disposed between said leading ends in parallel, coplanar relation thereto, and a hollow, hemispherical protuberance formed in a top surface of said flexible platform member, and further comprising a plurality of complementally formed protuberances formed in a top surface of said flat plate in linear array so that said flexible shield means is lookable into a plurality of functional positions of adjustment relative to a user's face.

7. The face shield of claim 4, further comprising a trailing flange formed in a trailing end of each of said flat member leading ends to inhibit rotation between said leading and trailing ends of said "L"-shaped flat members.

8. The face shield of claim 5, further comprising a clip means releasable mounted to said second bridge member, and a bias means for biasing said clip means to clampingly engage said pair of spectacle lens when said clip means is in repose so that said face shield is supported by said pair of spectacles.

9. The face shield of claim 8, wherein said clip means includes a pivotally mounted plate having a pair of transversely spaced apart depending legs, wherein said clip means includes a pair of lens-engaging members, each lens-engaging member of said pair of lens-engaging members being fixedly secured to an associated leg of said depending legs so that pivotal movement of said plate is imparted to said lens-engaging members, and said bias means biasing said plate and hence said lens-engaging members into engagement with said lens when said bias means is in repose.

10. The face shield of claim 9, wherein each of said lens-engaging means has a bulbous distal free end so that said lens are not scratched when said bias means is in repose.

11. The face shield of claim 1, wherein said shield means is clear.

12. The face shield of claim 1, wherein said shield means is tinted.

* * * * *